(12) United States Patent
Simpson (10) Patent No.: US 12,138,094 B2
(45) Date of Patent: Nov. 12, 2024

(54) DENTAL X-RAY RECEPTOR HOLDING DEVICE

(71) Applicant: Janet Thole Simpson, San Diego, CA (US)

(72) Inventor: Janet Thole Simpson, San Diego, CA (US)

(*) Notice: Subject to any disclaimer, the term of this patent is extended or adjusted under 35 U.S.C. 154(b) by 0 days.

(21) Appl. No.: 18/198,441

(22) Filed: May 17, 2023

(65) Prior Publication Data

US 2024/0188916 A1    Jun. 13, 2024

Related U.S. Application Data

(60) Provisional application No. 63/431,599, filed on Dec. 9, 2022.

(51) Int. Cl.
| | |
|---|---|
| *A61B 6/51* | (2024.01) |
| *A61B 6/00* | (2006.01) |

(52) U.S. Cl.
CPC ............ *A61B 6/512* (2024.01); *A61B 6/4423* (2013.01)

(58) Field of Classification Search
CPC ....... A61B 6/512; A61B 6/4423; A61B 6/425; G03B 42/042
See application file for complete search history.

(56) References Cited

U.S. PATENT DOCUMENTS

| | | | | |
|---|---|---|---|---|
| 7,972,060 | B2* | 7/2011 | Guichard | A61B 6/512 378/191 |
| 8,507,058 | B2* | 8/2013 | Motoyama | A61B 6/51 428/35.2 |
| 11,432,782 | B2* | 9/2022 | Spartiotis | A61B 6/512 |
| 2002/0067801 | A1* | 6/2002 | Gomez | G03C 3/003 378/169 |
| 2009/0232280 | A1* | 9/2009 | Tresso | A61B 6/512 378/169 |
| 2018/0064406 | A1* | 3/2018 | Pascal | A61B 6/512 |
| 2021/0030503 | A1* | 2/2021 | Shalev | A61C 9/0053 |

* cited by examiner

*Primary Examiner* — David P Porta
*Assistant Examiner* — Mamadou Faye
(74) *Attorney, Agent, or Firm* — Lee & Hayes, P.C.

(57) ABSTRACT

A holder for the dental x-ray image receptor which securely retains the digital image receptor for placement in a patient's mouth protecting the plastic barrier from rips or tears and cushioning the image receptor in the patient's oral cavity reducing pain associated with the placement of the image receptor. The dental x-ray holder, generally comprised of elastomeric material, stretches to fit various image receptors. The holder may be molded of one piece which may encase the perimeter of the image receptor encompassing all edges and corners providing an opening to receive the image receptor and accommodate the data cable. The holder may include appendages of varying hardness and density for positioning the image receptor to obtain bitewing and periapical images. This device may be used on its own or by means of slots in various orientations, adapted for use with other holding methods, devices and applications. It may also be simplified to a band encasing the perimeter.

20 Claims, 8 Drawing Sheets

DENTAL X-RAY RECEPTOR HOLDING DEVICE

BACKGROUND OF THE INVENTION

Cross Reference to Related Applications

This application claims priority from U.S. Provisional Patent Application No. 63/431,599, filed on Dec. 9, 2022, the contents of which is incorporated herein by reference.

FIELD OF THE INVENTION

The present disclosure relates to the field of dental radiography and more specifically to a dental x-ray digital image receptor holder and corresponding intraoral plastic barrier.

RELATED ART

The various aspects and embodiments of the invention described herein relate to the acquisition of dental x-rays. These images are obtained by means of x-radiation passing through the tissues of a patient's mouth onto an image receptor. Diagnostic quality intraoral radiographic images allow the dentist to diagnose carious lesions, apical infections, periodontal disease, some forms of oral cancer and many other conditions. In addition to their diagnostic value, radiographs are legal documents often presented as evidence in malpractice cases. It is crucial that dental auxiliaries obtain radiographs that meet the criteria for diagnostic quality. Therefore, the image receptor must be placed in the oral cavity with a degree of precision and held there stably. This can be challenging. Poor quality radiographs result in unnecessary exposure to ionizing radiation, missed diagnosis, and legal liability.

Dental professionals recognize the need for devices which hold the image receptor (such as film or digital sensor or phosphor plates) where it is placed in the mouth. U.S. Pat. No. 4,866,750A discloses a device for positioning dental x-ray image receptor within the mouth for producing x-ray images. The methods and devices used to position the image receptor adjacent to the teeth have evolved as technology has progressed over the years. Devices that held traditional film packets produced reliable results for decades. However, since the invention of the wired digital image receptor to produce digital x-ray images, those holding devices no longer sufficed. U.S. Pat. No. 6,652,141 is an example of a digital image receptor which is incorporated here for background purposes.

It has become more difficult to position the digital image receptor to obtain diagnostic quality x-rays with the digital image receptor comfortably and with stability. There are many reasons for this. The mouth is a very sensitive area, where approximately 19% of the body's sensory receptors are located. It is relatively small and has many structures (tongue, teeth, tori, frenum), that take space. The wired digital image receptor is hard, inflexible and bulkier than film making it more uncomfortable in the mouth. When patients are uncomfortable, they are less cooperative making the task of obtaining diagnostic quality radiographs much more difficult and time consuming.

In addition, the wired digital image receptor is considered a semi-critical device because it is used in the mouth and contacts the patients' saliva. It is always assumed that saliva may contain microscopic amounts of blood therefore may be capable of transmitting pathogens such as Hepatitis C and HPV (Human Papilloma Virus). Semi critical items must be sterilized. There are two ways to effectively sterilize semi critical instruments. They may be immersed in liquid glutaraldehyde for ten hours or run through a 20-to-30-minute cycle of steam under pressure in the autoclave. Neither of these methods is possible for the wired digital image receptor because it is highly sensitive electronic device and would not function if it were to go through either sterilization process. Therefore, a thin plastic barrier is relied upon to isolate and separate a patient's germs from the digital image receptor and subsequent patients. There are significant drawbacks to relying on thin plastic to perform this important function; The plastic barrier is slippery and becomes even more so when covered in saliva. As a result, the operator may position the digital image receptor in the patient's mouth with care, but the plastic barrier may cause the digital image receptor to slip out of the holder and the precise position the operator has placed it. The two sides of the plastic barrier are joined by a seam which forms a raised ridge. This seam can feel sharp and uncomfortable to the patient's thin oral mucosa. The plastic is often loose, and the extra material can irritate and activate the patient's gag reflex. Of higher importance the plastic barrier is also fragile. The plastic barrier may become scored or torn during the procedure, becoming antithetical to its purpose. Small holes in the plastic allow saliva to enter the barrier creating a risk of cross contamination between patients. Even if the operator wipes the digital image receptor down with disinfectant, that is not effective to kill tenacious and virulent pathogens which may harbor on the digital image receptor (example given: the reservoir formed by the junction of the digital image receptor and the data cable). When the digital image receptor is thus contaminated and used on a subsequent patient, and that plastic barrier gets a hole, saliva enters and exits the plastic and the previous patient's germs may be introduced to the current patient's system. There is a very real risk that disease may be transmitted in this manner. "U.S. Pat. No. 7,004,627 B2 discloses a barrier and cushioning apparatus for use with sensors as a means to avoid contamination of the sensor while providing improved comfort through the use of a cushion that may incorporate an integrated adhesive portion for securing to a positioning device such as a sensor holder".

Furthermore, traditional film packets are white, but the color of most digital image receptor is black or dark blue. The color matters because the inside of the mouth is dark. Without clear contrast, it is difficult to see a black or dark blue image receptor in the mouth especially when placing the digital image receptor in the visually obscured maxillary molar region.

A wide variety of dental x ray digital image receptor holders exist, and attempt to solve the issues of discomfort, and lack of stability.

U.S. Pat. No. 7,309,158, B2 a device attempting to address this problem. The plastic material and design are insufficient to fix that problem, instead it has introduced additional corners and bulk. However, there are problems with the existing sensor holders. The rigid structure of the sensor combined with the cable which connects the sensor to the computer dictates the manner that the sensor must be inserted into the sensor holding device. The requirement for holding the sensor in specific positions to obtain precise images are factors which limit how a sensor may be secured. The cable must be directed out of the patient's mouth. In most instances the side along which the cable exits the mouth becomes known as the anterior edge. No sensor holding device has succeeded in cushioning those corners because the rigid sensor must be inserted and removed from that side to obtain the periapical and bitewing images in the four quadrants of a patient's mouth. The anterior edge and adjacent corners often contact the thin sublingual oral mucosa, causing most patients significant discomfort. Edge ease U.S. Pat. No. 5,784,433A is a product that has long been used to cushion the edge of dental x-ray film. It has a smooth texture that is comfortable in the mouth. However, when moving the sensor to different quadrants within the mouth, the Styrofoam must be repositioned while taking a full mouth series of x-rays. Edge ease is fastened with adhesive which has a tendency to rip the plastic barrier when the operator pulls it off to reposition it. In addition, the Styrofoam material does not conform to the shape of the sensor resulting in added bulk further irritating the patients' tissues. Styrofoam cushioning sheaths (U.S. Pat. No. 9,643, 355 B2) have extended corners and add bulk to the mouth triggering a patient's gag reflex. Padded foam bite tabs or Styrofoam bite tabs do nothing to alleviate patient discomfort. The biting surfaces of the teeth do not need a cushion the mucosa does. These do not prevent the anterior corners of the sensor from offending the patients' tissues. The comfort wand encircles the perimeter of the x-ray sensor but does not effectively retain the sensor. The sensor slips out of the wand easily due to the inelasticity of the material. In addition, its only application is as a wand. It is not designed for use taking bitewings or periapical images using the paralleling technique. Neither the sensor cushion, JP2007001194U or the sensor protector KR200303670Y1 have appendages or bite tabs for holding the sensor in position. No sensor holding device seeks to protect the integrity of the plastic barrier. Rather when inserting the sensor into the device some of these devices cause tears and holes.

Previous sensor holding devices designed for positioning the sensor for bitewings and periapical x rays are insufficient to: cushion the hard bulky sensor, improve the visibility for the operator, and are not custom encased by a material that is soft and smooth with all the corners rounded, none is of elastomeric material that stretches to contain the sensor and plastic barrier yet compresses the barrier to be as compact and imperceptible as possible, and none provides protection to improve the integrity of the barrier with durable material such as silicone. Accordingly, there is a need in the art for an improved holding device for holding an image receptor for dental x-rays.

SUMMARY OF THE INVENTION

Summary of the Invention

It is therefore the objective of this invention to provide a digital image receptor holding system to address:

The discomfort caused by the bulk of the digital image receptor given the lack of space in the mouth.

The discomfort caused by the hardness of the digital image receptor contacting the sensitive oral mucosa.

The deficiencies of the plastic barrier to provide adequate protection from disease transmission.

The hindrance of the plastic barrier to securely retain the digital image receptor in the holding device.

The poor visibility of the dark colored digital image receptor in the naturally dark mouth.

Comfort: This invention is made of soft, smooth, radiolucent, and elastomeric material which encases the digital image receptor on the surfaces that touch the patient's sensitive oral mucosal tissues. The material may be made of silicone, rubber, or other similar materials. The elastomeric nature of the material of this invention is unique in that it allows for the coverage and cushioning of every corner. The device encases the recording surface, all four sides, twelve edges and eight corners of the digital image receptor. The material extends partially around the side where the data cord is connected to the digital image receptor. Excess plastic from loose fitting barriers is compressed within the Sensorskinz holding device which reduces the perception of added bulk felt in the mouth.

Safety: This invention envelopes and improves the infection prevention integrity of the plastic barrier protecting it from rips and tears. The device touches human saliva and other potentially infectious material, therefore it must either tolerate the temperature and pressure of the autoclave or be sterilized in cold sterile. Alternatively, it may be disposable.

Stability and functionality: This invention contains the digital image receptor securely. It is made to fit the smallest digital image receptor and stretches to fit even the largest size of wired digital image receptors. The slippery surface of the plastic is covered which allows the digital image receptor to be held reliably where it is placed in the mouth. Bite tabs are required to take bite wing and periapical x-rays using the paralleling technique. Bite tabs made from a variety of rigid materials such as polyethylene may be integrated into the device, fabricated as one unit with the silicone image receptor skin perimeter in a plurality of positions and orientations to procure the required images. Alternatively, slots can be made in the fabric of the Sensorskinz holding device relative to the position of the Bite tabs of other sensor holding devices know in the industry. The Sensorskinz holding device can be slipped over the existing sensor holder through the slot in this manner the existing holding device has improved stability, retention and patient comfort.

Visibility: In addition, the color of the device appears white, but is not limited to white. Slight shades of radiolucent pigment may be used to quickly differentiate between the types of holders.

BRIEF DESCRIPTION OF DRAWINGS

The features of the present invention can be more readily understood with the drawings herein and accompanying description.

FIGS. 3A-3D are perspective views showing a holding device (10A) for obtaining bitewing x-rays in a vertical orientation.

FIG. 6A is a perspective rear view showing a backplate surface (9c) of a holding device (10C) with a slot (8c) cut out to accommodate a rigid bite tab of an image receptor (20C)

in the holding device (10C) for obtaining horizontal bite wing x-rays.

DETAILED DESCRIPTION

Figure 2:
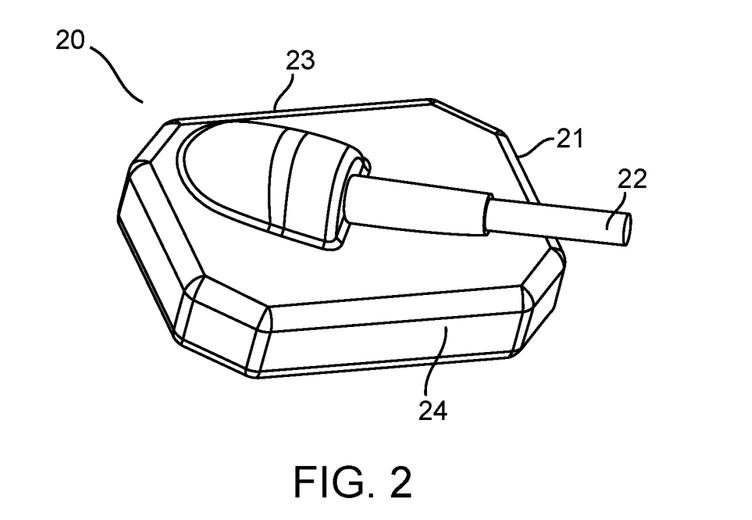
FIG. 2 is a perspective view showing digital dental x-ray image receptor (20) used to obtain intraoral dental x-rays having an anterior edge of the image receptor (21), a data cable (22), a first side edge (23) of the image receptor (20), and opposite second side edge (24) of the image receptor (20).
Figure 3A:
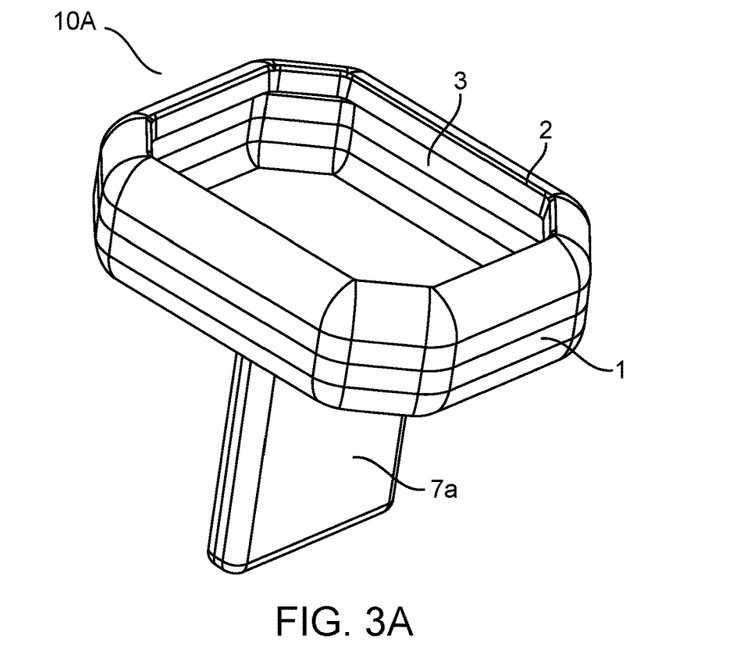
Figure 3B:
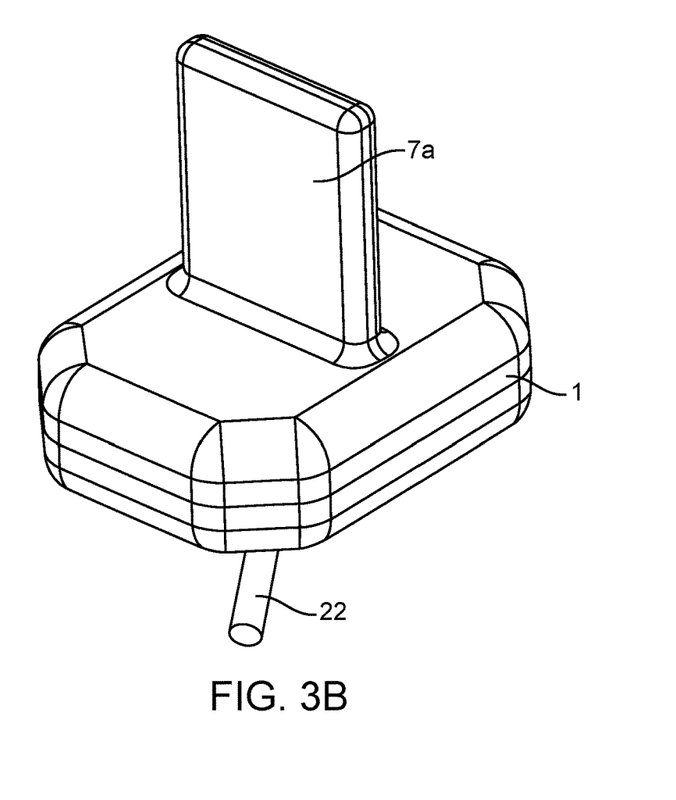
Figure 3C:
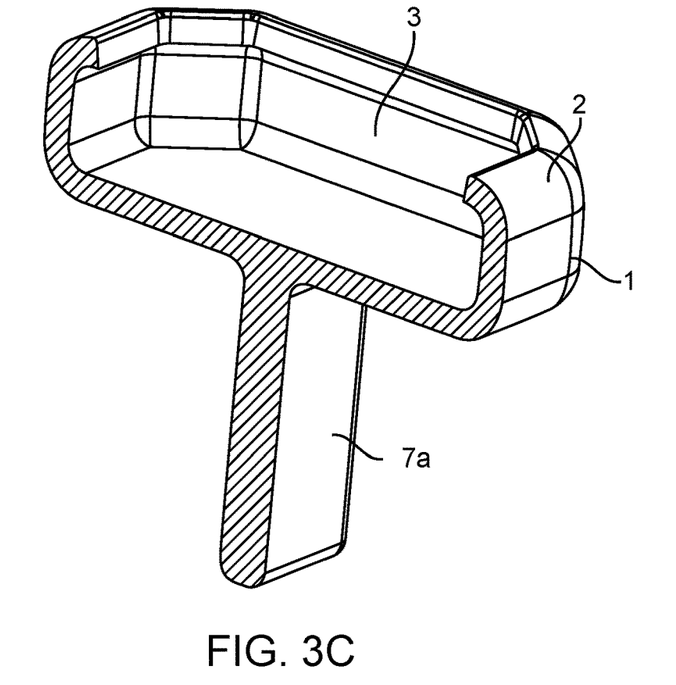
Figure 3D:
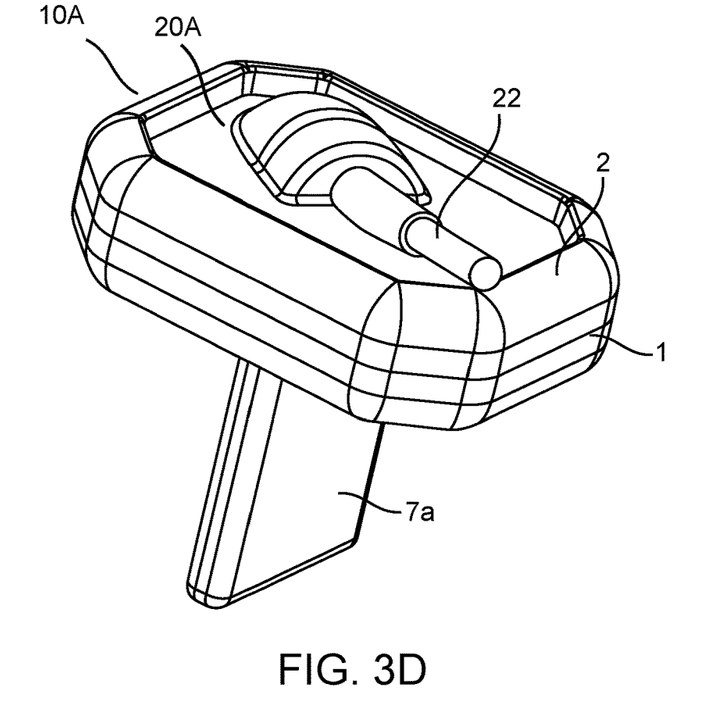
FIG. 3D shows an image receptor (20A) inserted in the holding device (10A).
Figure 4:
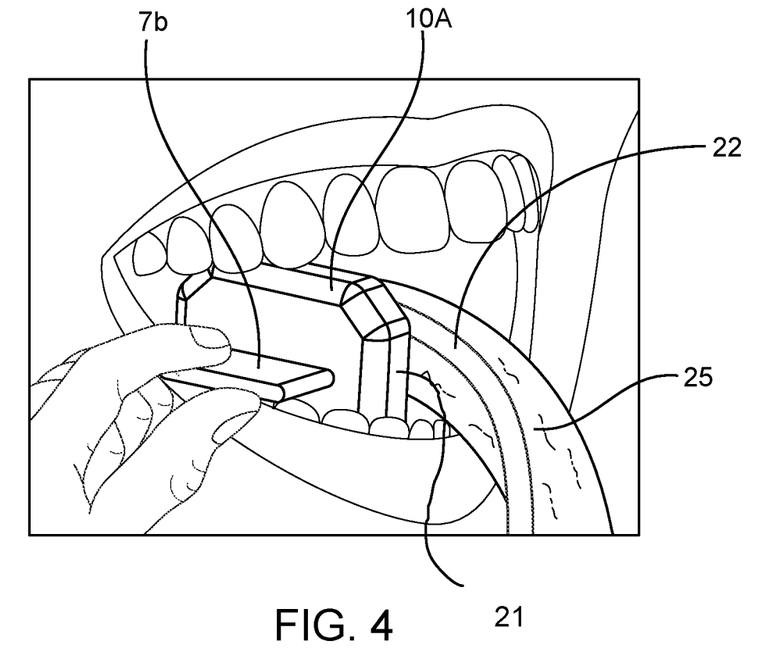
FIG. 4 is a perspective view showing the holding device (10A) inserted in the human mouth for obtaining horizontal bitewing x-rays including a cushioned perimeter band (1), the data cable (22), a bite tab (7a), and a plastic barrier (25).
Figure 5A:
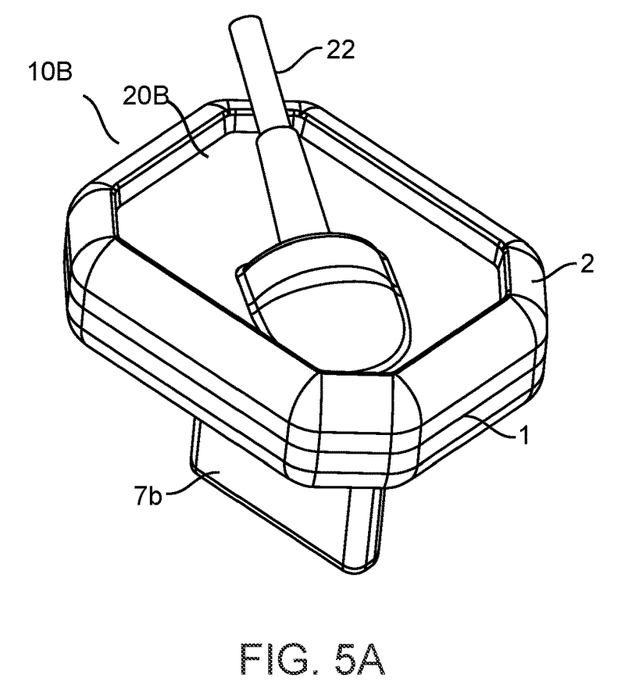
FIGS. 5A, 5B are perspective views showing a holding device (10B) the bitetab (7b) is positioned for obtaining bitewing x-rays in a horizontal orientation. Shows an image receptor (20B) inserted in the holding device(10B).
Figure 5B:
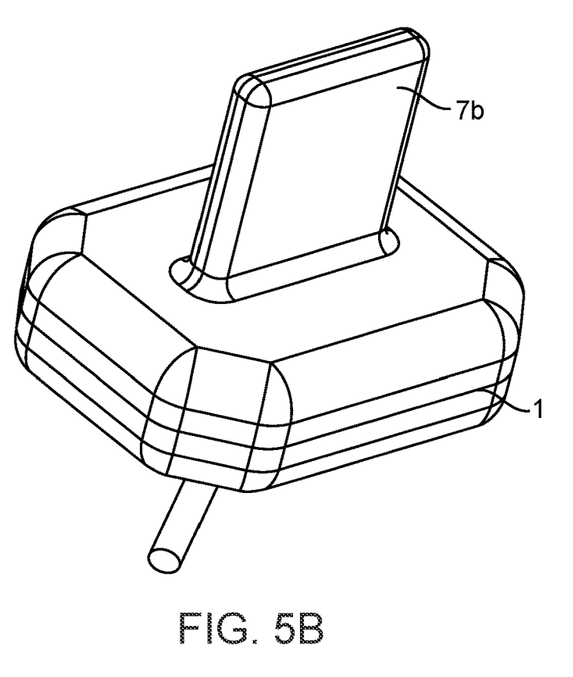
Figure 6A:
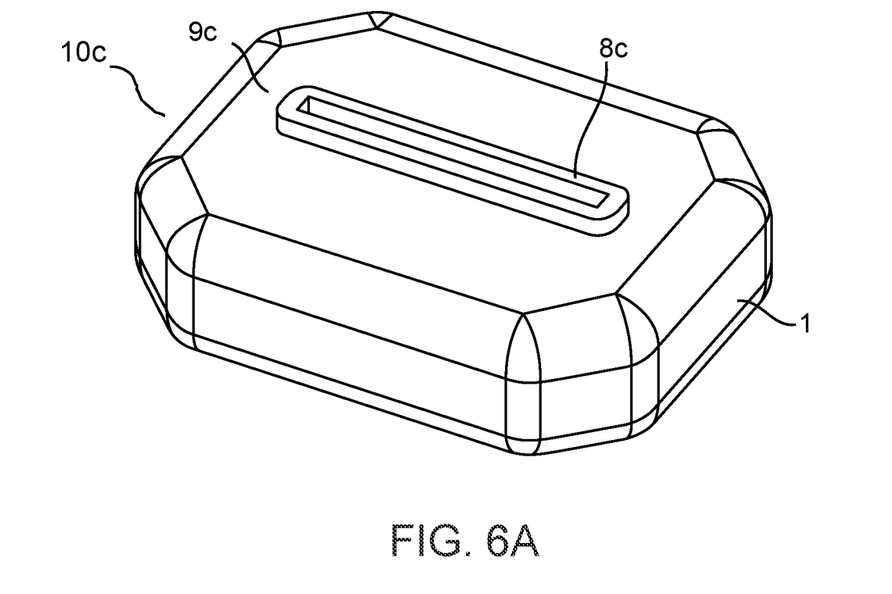
Figure 6B:
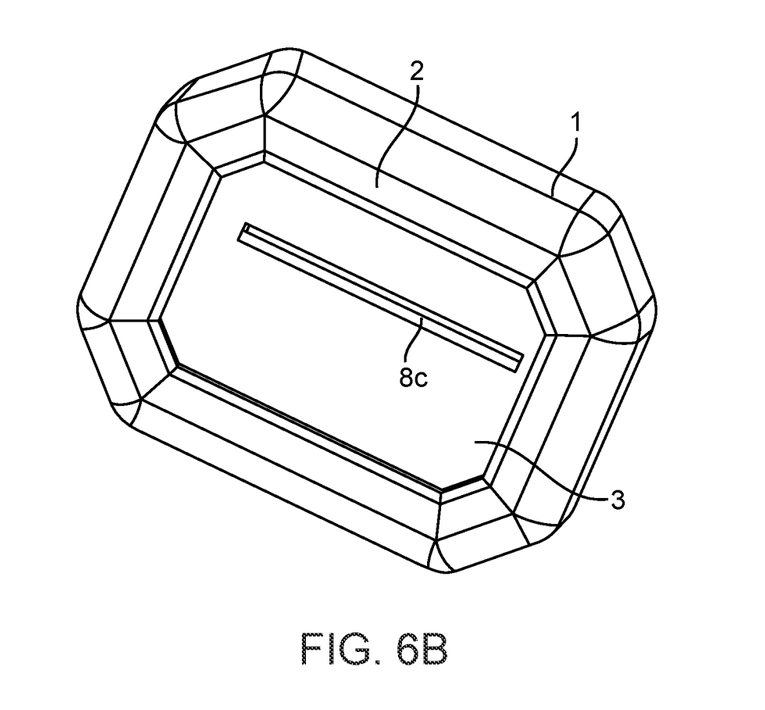
FIG. 6B is a perspective front view showing the backplate surface (9c) with the opening (3) to receive the image receptor (20C) and the marginal flange (2) extending inwardly to retain the image receptor (20C).
Figure 7:
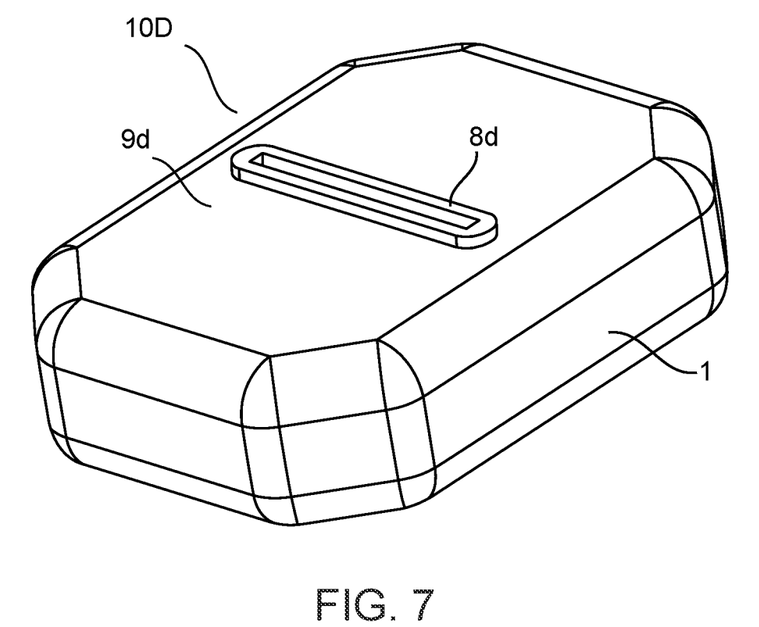
FIG. 7 is a perspective rear view showing a holding device (10D) with a slot (8d) cut out to accommodate a rigid bite tab of an image receptor (20D) oriented for obtaining vertical bitewing images.

To obtain diagnostic quality dental x-rays, dental personnel must place the digital image receptor (FIG. 2) in precise positions in the patients' mouths, then project an x-ray beam through the teeth to the digital image receptor. A full mouth series of dental x rays is usually a combination of 14 periapical x-rays and 4 bitewing x-rays. A periapical x-ray is an image of each tooth from the crown to the tip of each root. It is well to have three millimeters of tissue visible beyond the apices so the dentist can see the health condition of the teeth, periodontal ligament, and alveolar bone. A bite wing x-ray is an image that shows the interproximal aspect of the maxillary and mandibular teeth as well as the alveolar bone level.

Figure 8:
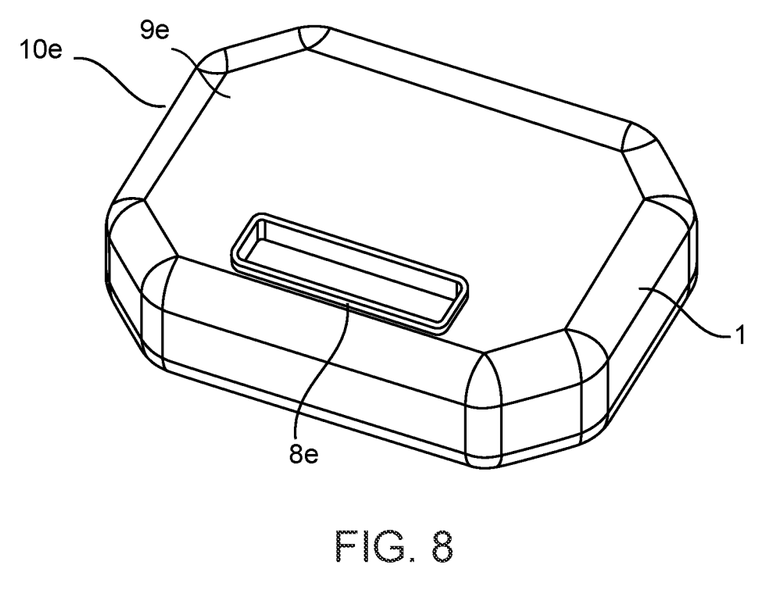
FIG. 8 is a perspective rear view showing a holding device (10E) with a slot (8e) cut out to accommodate a rigid bite tab of an image receptor (20E) oriented for obtaining posterior periapical images.
Figure 9:
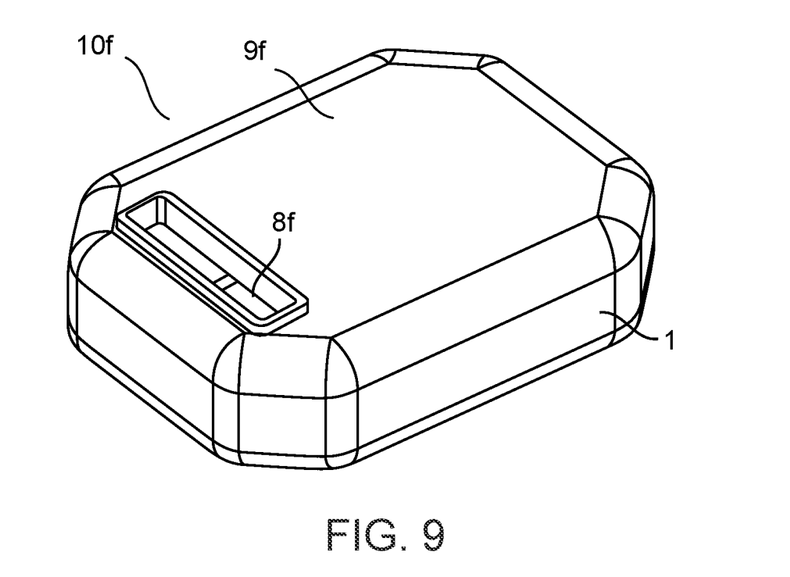
FIG. 9 is a perspective rear view showing a holding device (10F) with a slot (8F) cut out to accommodate a rigid bite tab of an image receptor (20F) oriented for obtaining anterior periapical images.
Figure 10:
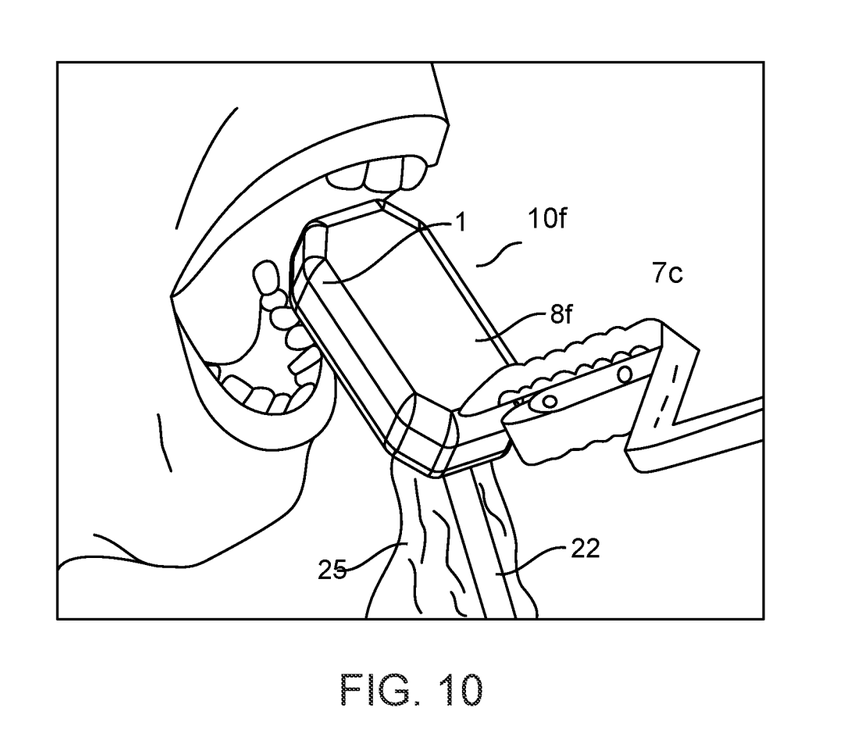
FIG. 10 is a perspective view showing the placement of a holding device (10) in the human mouth with a cushioned perimeter (1), the data cable, (24) and slot 8f to accommodate the image receptor (20F) bite tab (9f) plastic barrier (25).

When taking a full mouth series of x-rays with the wired digital image receptor (20) (FIG. 2) using the paralleling technique, the operator usually performs the task in the following sequence. One begins by placing a plastic barrier (25) (FIGS. 4-7) over the digital image receptor (20) and the data cable (22). The digital image receptor (20) and plastic barrier (25) are placed inside a Sensorskinz holding device (10E) (FIG. 8) configured for posterior periapical images. A first side edge (23) is directed toward a bite tab (7) which corresponds to the occlusal surfaces of the patient's teeth. The recording surface of the digital image receptor is placed against a back (9) of space (3) of the Sensorskinz holding device and placed adjacent to the maxillary molar teeth. An anterior edge (21) and a data cable (22) are situated so as to direct the cable out of the patient's mouth. Images are taken in the maxillary right molar region and the maxillary right premolar region. The digital image receptor is rotated, and images are taken of the mandibular left molars, then mandibular left premolars. At that point the operator must remove the digital image receptor (20) from the Sensorskinz holding device (10) and convert the device to an orientation to take images of the other two quadrants, then reinsert the digital image receptor (20) into the Sensorskinz holding device (10). In essence the digital image receptor (20) must be flipped. A second side (24) is now on the side of the bite tab (7). The anterior edge (21) of the digital image receptor (20) and the data cable (22) are repositioned so that the cable is directed out of the patient's mouth. The digital image receptor (20) is placed in the mouth to capture the maxillary left molar, then the maxillary left premolar images. The device is rotated and placed to obtain images of the mandibular right molars and then the mandibular right premolars. At that point the operator removes digital image receptor from the holding device(10E) and places it into a Sensorskinz holding device designed to obtain images of the anterior teeth (10F) (FIG. 9). The anterior edge (21) and the data cable (22) is directed toward the bite tab (7c) which corresponds to the incisal edge of the teeth and out of the mouth. The six images, three on the maxillary and three on the mandibular, may be obtained without reorienting the digital image receptor in the device. Then the digital image receptor is removed from the anterior holding device and placed in a device to obtain the bitewing images (10A, 10B, 10C, or 10D) may be used for this purpose. For a bitewing projection the dental personnel must place the digital image receptor (20) in the sulcus between the patient's teeth and the tongue, and place the bite tab (7A or 7B) on the occlusal surface of the molar and premolar teeth respectively. The patient will close their jaws to retain it in place. Then they project the x-ray beam through the contacts of the molar and premolar teeth, creating an image.

When taking a full mouth series of x-rays using the bisecting technique, the operator begins by placing a plastic barrier (25) over the digital image receptor (20) and the data cable (22). The digital image receptor and plastic barrier are placed inside the SnapJack with the rigid edge corresponding to edge of the digital image receptor. The SnapJack is then placed inside the jaws of the Snap-a-ray U.S. Pat. No. 8,641,275B2.

Previous holding devices did nothing to contain the corners and sharp seam of the plastic barrier. When placing the digital image receptor in the maxillary molar region it is common to trigger the gag reflex with the corner of the plastic barrier. The Sensorskinz holding device envelope the irritating plastic and compress the plastic barrier keeping the bulk of the device as compact as possible. Patients often complain that the hard bulking digital image receptor hurts their palate. The Sensorskinz holding device cushions the hard edges (FIGS. 2 5 & 6) with soft rounded edges that are smooth.

Figure 1:
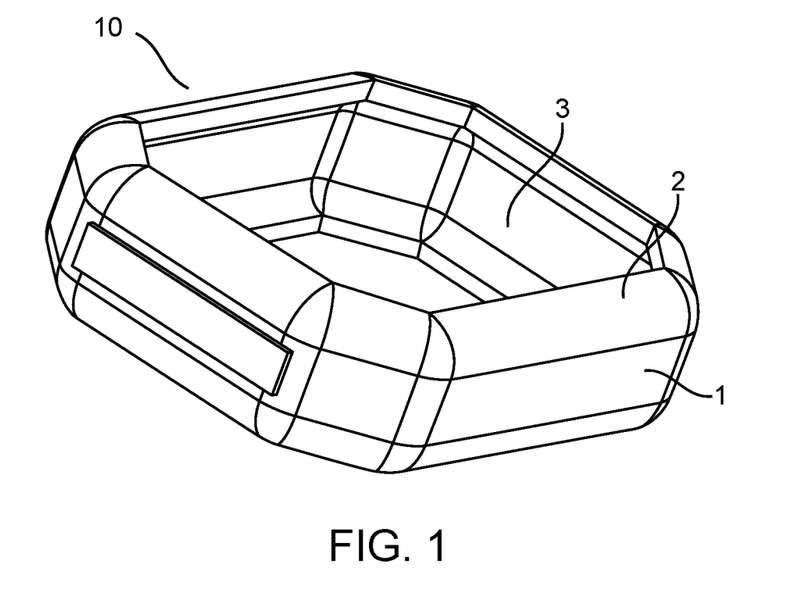
FIG. 1 is a perspective view showing a holding device 10 having a cushioned perimeter band, (1) a marginal flange (2), and space (3) for a image receptor (20).

When placing the digital image receptor to obtain the mandibular premolar region previous holding devices allowed the hard anterior edges of the digital image receptor to irritate the thin sublingual mucosa. The Sensorskinz holding device unique opening combined with the elastomeric material allows for covering the anterior edges by inserting the digital image receptor into the Sensorskinz holding device via an opening (FIG. 1,3), rather than the anterior side.

Previously when taking a periapical x-ray with the Snap-a-ray it was common for the digital image receptor to slip out of the snap a ray due to the slippery plastic barrier. In addition, 0.5 cm of recording surface was lost due to the way it was previously held in the snap a-ray. The Snapjack (drawing not included) provides a stable nonslip edge which allows the snap a ray to secure the digital image receptor. The SnapJack "jacks up" the digital image receptor by providing a 0.5 cm rigid edge that elevates the digital image receptor from the jaws of the snap a ray recovering the lost recording surface.

The invention claimed is:

1. A holding device for obtaining dental x-rays using an image receptor, the holding device comprising:
    a backplate surface sized to correspond with a shape and size of the image receptor;

a wall extending from, and transversely to, the backplate surface, the wall surrounding a perimeter of the backplate surface; and a marginal flange extending inwardly from a side of the wall opposite the backplate surface so as to extend over at least a portion of the backplate surface, thereby defining a receptacle to removeably receive the image receptor, wherein the wall and the marginal flange are formed of an elastomeric material such that:

the wall and the marginal flange stretch out and around the image receptor to removeably receive the image receptor in the receptacle, and subsequent to the image receptor being removeably received in the receptacle, the wall and marginal flange constrict onto the image receptor to retain the image receptor in the receptacle such that a front side of the image receptor abuts the backplate surface, and a rear side of the image receptor abuts the marginal flange.

2. The holding device of claim 1, wherein the elastomeric material comprises silicone rubber.

3. The holding device of claim 2, further comprising a plastic barrier disposed around the image receptor, a data cable junction, and at least a portion of a data cable, and subsequent to the image receptor being removeably received in the receptacle, the wall and marginal flange constrict down onto both of the plastic barrier and the image receptor to retain the plastic barrier and image receptor in the receptacle, wherein the elastomeric material does not score or tear the plastic barrier.

4. The holding device of claim 1, wherein the backplate surface is a first backplate surface, and further comprising:
a second backplate surface opposite the first backplate surface; and one or more bite tabs,
wherein the one or more bite tabs are formed of one piece with the second backplate surface,
wherein the one or more bite tabs are affixed to the second backplate surface, or wherein one or more slots may be cut out of the first backplate surface and the second backplate surface to accommodate the one or more bite tabs.

5. A holding device for holding an image receptor obtaining dental x-rays comprising:
a backplate surface sized to correspond with a shape and size of the image receptor;
a wall extending from, and transversely to, the backplate surface, the wall surrounding a perimeter of the backplate surface; and
a marginal flange extending inwardly from a side of the wall opposite the backplate surface so as to extend over at least a portion of the backplate surface, thereby defining a receptacle to removeably receive the image receptor,
wherein the wall and the marginal flange are formed of an elastomeric material such that the wall and marginal flange constrict onto the image receptor to retain the image receptor in the receptacle such that a front side of the image receptor abuts the backplate surface, and a rear side of the image receptor abuts the marginal flange.

6. The holding device of claim 5, further comprising a plastic barrier disposed around the image receptor, a data cable junction, and at least a portion of a data cable, and subsequent to the image receptor being removeably received in the receptacle, the wall and marginal flange constrict down onto both of the plastic barrier and the image receptor to retain the plastic barrier and image receptor in the receptacle.

7. The holding device of claim 6, wherein the elastomeric material comprises silicone or rubber.

8. The holding device of claim 5, wherein the wall and the marginal flange stretch out and around the image receptor to removeably receive the image receptor in the receptacle.

9. The holding device of claim 5, wherein the backplate surface is made of the elastomeric material.

10. The holding device of claim 5, wherein the backplate surface is a first backplate surface, and further comprising:
a second backplate surface opposite the first backplate surface; and
one or more bite tabs,
wherein the one or more bite tabs are formed of one piece with the second backplate surface, or
wherein the one or more bite tabs are affixed to the second backplate surface.

11. The holding device of claim 10, wherein the first backplate surface and the second backplate surface are formed of polyethylene.

12. The holding device of claim 11, wherein the one or more bite tabs are formed of polyethylene.

13. The holding device of claim 10, wherein the first backplate surface and the second backplate surface are formed of the elastomeric material.

14. The holding device of claim 5, wherein the backplate surface is a first backplate surface, and further comprising:
a second backplate surface opposite the first backplate surface; and
one or more bite tabs,
wherein one or more slots may be cut out of the first backplate surface and the second backplate surface to accommodate the one or more bite tabs.

15. A holding device for holding an image receptor obtaining dental x-rays comprising:
a backplate surface sized to correspond with a shape and size of the image receptor;
a wall extending from, and transversely to, the backplate surface, the wall surrounding a perimeter of the backplate surface; and
a marginal flange extending inwardly from a side of the wall opposite the backplate surface so as to extend over at least a portion of the backplate surface, thereby defining a receptacle to removeably receive the image receptor,
wherein the wall and the marginal flange are formed of an elastomeric material such that the wall and the marginal flange stretch out and around the image receptor to removeably receive the image receptor in the receptacle.

16. The holding device of claim 15, wherein the elastomeric material comprises silicone or rubber.

17. The holding device of claim 15, wherein the backplate surface is formed of polyethylene.

18. The holding device of claim 15, wherein the backplate surface includes one or more bite tabs extending outwardly from the backplate surface.

19. The holding device of claim 15, wherein the backplate surface includes one or more slots to accommodate one or more bite tabs.

20. The holding device of claim 15, wherein the backplate surface is a first backplate surface, and further comprising:
a second backplate surface opposite the first backplate surface; and
one or more bite tabs, wherein one or more slots may be cut out of the first backplate surface and the second backplate surface to accommodate the one or more bite tabs.

* * * * *